United States Patent

Widlund et al.

[11] Patent Number: 5,817,085
[45] Date of Patent: *Oct. 6, 1998

[54] METHOD FOR THE MANUFACTURING OF AN ABSORBENT STRUCTURE AND AN ABSORBENT ARTICLE

[75] Inventors: Urban Widlund, Mölnylycke; Eje Österdahl, Västra Frölunda; Roy Hansson, Mölndal; Milan Kolar, Sundsvall, all of Sweden

[73] Assignee: SCA Mölnlycke AB, Gothenburg, Sweden

[ * ] Notice: The term of this patent shall not extend beyond the expiration date of Pat. No. 5,728,085.

[21] Appl. No.: 436,275

[22] PCT Filed: Nov. 15, 1993

[86] PCT No.: PCT/SE93/00971

§ 371 Date: May 16, 1995

§ 102(e) Date: May 16, 1995

[87] PCT Pub. No.: WO94/10953

PCT Pub. Date: May 26, 1994

[30] Foreign Application Priority Data

Nov. 17, 1992 [SE] Sweden .................................. 9203445

[51] Int. Cl.$^6$ ................. A61F 13/15; D03D 3/00
[52] U.S. Cl. ................. 604/379; 604/375; 604/369; 428/224
[58] Field of Search .................................. 604/368, 375, 604/378, 385.1, 379, 369, 367; 156/62.2; 425/80.1–82.1, 84; 428/224, 225, 236, 237, 240

[56] References Cited

U.S. PATENT DOCUMENTS

| 4,327,728 | 5/1982 | Elias | 604/904 |
|---|---|---|---|
| 4,507,122 | 3/1985 | Levesque . | |
| 4,610,678 | 9/1986 | Weisman et al. | 604/378 |
| 4,898,642 | 2/1990 | Moore et al. | 604/375 |
| 5,134,007 | 7/1992 | Reising et al. | 604/385.1 |
| 5,324,575 | 6/1994 | Sultze et al. | 424/224 |

FOREIGN PATENT DOCUMENTS

| 0202472A1 | 11/1986 | European Pat. Off. . |
|---|---|---|
| 0251675A2 | 1/1988 | European Pat. Off. . |
| 0255654A1 | 2/1988 | European Pat. Off. . |
| 0360472A2 | 3/1990 | European Pat. Off. . |
| 0523744A1 | 1/1993 | European Pat. Off. . |
| 468 744 | 3/1993 | Sweden . |
| 2140471 | 11/1984 | United Kingdom . |
| 9005808 | 5/1990 | WIPO . |
| WO 90/05808 | 5/1990 | WIPO . |

*Primary Examiner*—Mary Beth Jones
*Assistant Examiner*—David J. Cho
*Attorney, Agent, or Firm*—Burns, Doane, Swecker & Mathis LLP

[57] ABSTRACT

A method for the manufacturing of an absorbent structure in an absorbent article, such as a sanitary napkin, tampon, panty protector, wound or sore dressing and like articles is produced by using absorbent material in roll form directly in the product without first defibrating the material and then forming a mat. The material possesses good dispersion properties and swelling properties, which are meaningful to the function of the product. A high surface dryness is obtained, among other things. In addition to cellulose fibers, the absorbent structure may also include superabsorbent material and/or binding fibers, among other ingredients. The pulp mat is very thin, therewith obviating the need to compress the mat further in the product. In the case of certain product applications, the material is softened mechanically prior to its use as an absorbent material.

22 Claims, 2 Drawing Sheets

METHOD FOR THE MANUFACTURING OF AN ABSORBENT STRUCTURE AND AN ABSORBENT ARTICLE

BACKGROUND

1. Field of the Invention

The present invention relates to a method for manufacturing of an absorbent structure in an absorbent article, such as a sanitary napkin, a tampon, a panty protector, a wound or sore dressing and like articles. The invention also relates to an article manufactured according to the method.

2. Discussion of Related Art

Many different types of absorbent articles of this kind are known to the art. The absorbent bodies of such articles are typically produced by dry-defibering and fluffing cellulose pulp in roll, bale or sheet form for instance, to form a pulp mat, sometimes admixed with so-called superabsorbent material in the pulp mat, these absorbents being polymers which are capable of absorbing many times their own weight of water or body fluid.

The pulp body is often compressed so as to enhance its fluid-dispersion ability and also in order to reduce pulp body bulk and therewith obtain an article which is as compact as possible.

The absorbent body may also include other constituents, for instance constituents which will improve its fluid-aquisition properties or its fluid-wicking properties, or which will increase its coherent strength, i.e. its coherency, and its ability to withstand deformation in use.

One serious drawback with products of this nature is found in the total absorption capacity of the articles and also in the fact that the articles will often leak long before their total absorption capacity has been fully utilized. Among other things, this is because the body fluid discharged by the wearer is unable to penetrate into the absorption material and to spread to hitherto unused areas of the article quickly enough, but instead leaks from the sides of the sanitary napkin or the wound dressing. The ability of the materials used in the article to disperse the absorbed fluid throughout the entire absorbent body is thus highly important.

Another problem resides in so-called rewetting, i.e. the transference of body fluid that has already been absorbed back into contact with the wearer's skin as a result of external forces, for instance when the wearer sits down. It is generally desired that the surface of the article that lies proximal to the wearer in use will remain as dry as possible.

Another desideratum with regard to the majority of hygiene products is that the article shall be thin, so that it can be worn as discretely as possible.

A very large part of the production plants used in the manufacture of the aforesaid hygiene articles is comprised of defibrating equipment, pneumatic conveying systems and mat-forming equipment. This equipment is also the source of serious faults in the production plants. Equipment for compressing the finished pulp mat or the finished hygiene product is furthermore often included downstream of the production plants.

It is known from International Patent Application WO 90/05808 to produce a pulp web by dry-forming, which is later defibered, so-called dry-formed roll or reel pulp. Flash-dried paper-pulp fibers, which may consist of thermomechanical pulp, chemi-thermomechanical pulp, CTMP, or chemical paper pulp, sulphite or sulphate pulp with a dry solids content of about 80% is delivered by means of an air stream in a controlled flow to a forming head arranged above a forming wire and there formed into a web that has a weight per unit area of 300–1500 g/m2 and a density of 550–1000 kg/m3. Air is sucked away through a suction box placed beneath the wire. The moisture content in the process shall be 5–30%.

The web is pre-pressed to a density of 550–1000 kg/m3 in order to slightly reduce the bulk of the web prior to the final pressing stage. The pressed web has a mechanical strength which enables the web to be rolled-up or handled in sheet form for storage and transportation purposes. The web can be readily defibered and is intended to be converted into fluff for use in the manufacture of absorbent bodies or pads for diapers, sanitary napkins and like articles.

Another method for the manufacturing of an absorbent structure is described in European Patent 0 122 142, where a mixture of hydrophilic fibers and water insoluble particles of insoluble hydrogel is airlaid into a web and compressed to a density of 0.15 to about 1.0 g/cm2. This method however comprises several production steps, where the dry lap base material is first disintegrated into cellulose fibers by use of a hammer mill, whereafter the fibers are deposited on a screen surface and formed to the absorbent structure, which is then compressed. These manufacturing steps make this process rather complicated and expensive.

SUMMARY AND OBJECTS

An object of the present invention is to provide in an absorbent article of the aforedescribed kind an absorbent structure which exhibits extremely good absorption properties, both with respect to its ability to quickly take up fluid and also with respect to its ability to spread fluid throughout the material. The material will preferably exhibit low rewetting tendencies as well as being capable of being made very thin. It is also desired to provide a simplified method of manufacturing absorbent articles of the kind defined in the introduction. These objects and desiderata are achieved with a manufacturing method in which particulate material comprising 30–100%, preferably at least 50% and most preferably at least 70% flash-dried cellulose fibers is dry-formed to a web with a weight per unit area of between 50–500 g/m2 and compressed to a density of between 0.2–1.0 g/cm3 and that the web without subsequent defibration and fluffing is incorporated as an absorbent structure in an absorbent article.

Non-defibered, dry-formed roll pulp has been found to be an extremely good absorption material and can be used directly as an absorbent material in hygiene articles, without being defibered. The material also has good fluid dispersion properties and swelling properties, which are meaningful to the function of the product. The pulp mat is very thin and therefore need not be further compressed in the product or article.

In the case of certain product applications in hygiene articles, it is convenient to soften dry-formed roll pulp prior to its use as an absorption material. The earlier mentioned good absorption properties, fluid wicking properties and swelling properties are not influenced by the softening process to any great extent. One method to soften an absorbent sheet is described in European Patent Application EP 0 360 472, where the compressed absorbent material is worked between partially cutting rollers and thereby gaining softness. This method however leads among other things to decreased strength in the softened material.

BRIEF DESCRIPTION OF THE DRAWINGS

The invention will now be described in more detail with reference to a number of exemplifying embodiments thereof and also with reference to the accompanying drawings, in which.

DETAILED DESCRIPTION OF THE PREFERRED EMBODIMENTS

Figure 1:
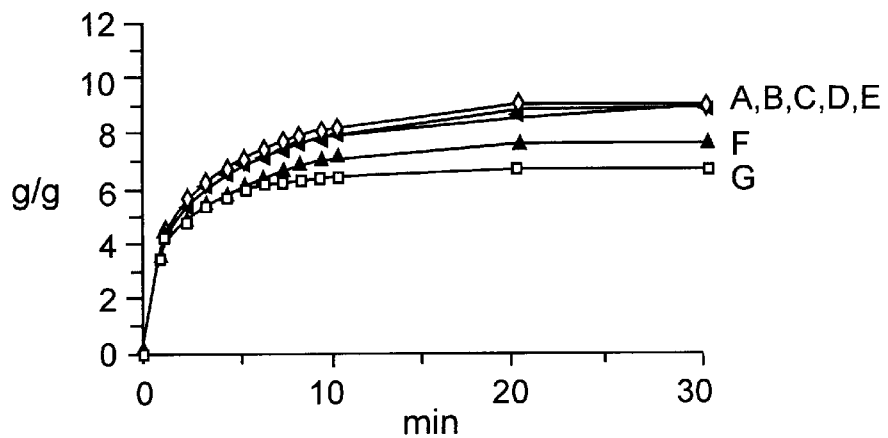
FIG. 1 illustrates the absorption properties of a dry-formed CTMP-material subsequent to being worked between rolls at different roll spacings. Conventionally formed and compressed pulp mats of CTMP-pulp and chemical pulp respectively were used as references.

Important properties of a material used in the manufacture of a hygiene article are its absorbent capacity, absorption rate, dispersion capacity, drainage capacity, retention capacity, rewetting, softness and smoothness.

The fluids concerned are menstruation blood, blood and fluid matter from wounds and sores.

An object of the present invention is to provide in an absorbent article such as a sanitary napkin, tampon, panty protector, wound or sore dressing and like articles, an absorbent structure which exhibits highly effective absorption properties, both with regard to its fluid-aquisition rate and its ability to disperse fluid throughout the material. The material will also preferably have low rewetting and be capable of being made very thin and smooth. It is also desired to simplify the manufacturing process. A finished absorbent material in roll form which can be used without needing to be defibered would partially reduce the need for the earlier mentioned defibering equipment, pneumatic conveying systems and mat-forming equipment, and consequently there is a demand for such material.

The aforesaid objects and desiderata have been achieved in accordance with the invention by including in the absorbent structure that is manufactured by a method in which particulate material comprising 30–100%, preferably at least 50% and most preferably at least 70% flash-dried cellulose fibers is dry-formed to a web with a weight per unit area of between 30–2000 glm2 and compressed to a density of between 0.2–1.0 g/cm3 and that the web without subsequent defibration and fluffing is incorporated as an absorbent structure in an absorbent article.

In accordance with the invention, there is used a dry-formed product which is manufactured from particulate material as mechanical pulp or chemi-thermomechanical pulp (CTMP) or a corresponding product manufactured from sulphite pulp or sulphate pulp, so-called chemical cellulose pulp. Cellulose fibers which have been stiffened chemically may also be used. In the dry-formed product can also be included other particulate matter as superabsorbents, thermoplastic binding fibers and other kind of fibers.

Non-treated dry-formed roll pulp has extremely good absorption, dispersion and swelling properties, and it has been found possible to use the material immediately as an absorption material in hygiene articles without defibrating the pulp. In the case of certain absorbent articles, it has been found suitable to soften the material slightly prior to its use. One method of softening the material is described below.

Dry-formed cellulose pulp can be produced, for instance, by forming a web of flash-dried paper pulp fibers in accordance with the method described in International Patent Application WO 90/05808.

Cellulose pulp fibers have a so-called curl value which defines the crookedness of the fiber. Curl'value can be measured according to the method described by B. D. Jordan, N. G. Nguyen in Papper och Trä4/1986, page 313. An embodiment of the present invention has a curl-value of between 0.20 and 0.40.

Softening of the Material

The material can be given a softness which renders the material highly suitable for use as an absorption material in the majority of hygiene articles, by working dry-formed roll pulp between for instance corrugated rolls. The material can be brought to different degrees of softness for different product applications, by working the material between different types of rolls and at different roll spacings.

Dry-formed roll pulp which has been softened in this way exhibits very good product properties, and the earlier mentioned good absorption properties are not influenced by the softening process to any great extent.

Figure 6:
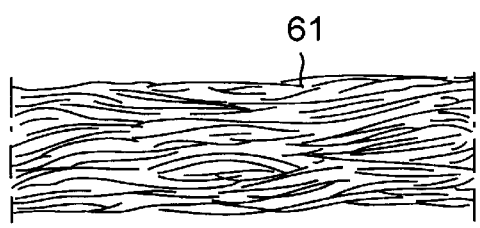
FIG. 6 illustrates the structure of a cross section of the material in unsoftened condition.
Figure 7:
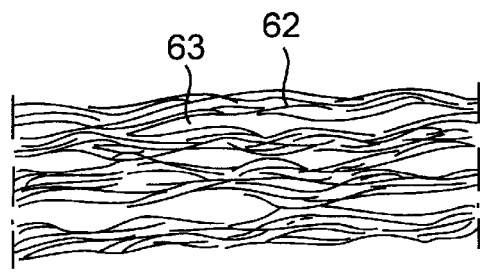
FIG. 7 illustrates the structure of a cross section of the material in softened condition.

The material is delaminated in the softening process as illustrated in FIGS. 6 and 7. The unsoftened material has normally an even high density throughout the whole the thickness of the material (61). As a result of the softening process the material is delaminated so as to form a plurality of partially separated (63), thin fiber layers (62).

Softening and delamination of the material reduces its total density to some extent, although the original density is essentially retained in each individual layer. Because a very high density is retained in the individual layers, the good fluid wicking properties of the material are retained despite the increase in bulk obtained in conjunction with the softening process. The total bulk is increased by up to 300%, normally 1–100%, as a result of the softening process, depending on the method used and the extent to which the material is softened.

It will be understood that the aforesaid material softening method has been given solely by way of example and that corresponding results can be achieved with the aid of other methods. For instance, the material could eventually be softened by means of ultrasonic energy, microwaves, by moisturizing the material, or with the aid of chemical additives.

Investigation of Material Properties

The test equipment described below was used to evaluate absorption properties.

Method 1. Absorption Properties Up an Inclined Plane

A rectangular test body was punched from the material and a line was drawn transversely across the test body at a point 11 cm from one short end of the body. A fluid container was placed adjacent laboratory scales and both the scales and the container were adjusted to a horizontal position. A plexiglass plate was placed on the scales at a 30° slope, with one free edge of the plate extending slightly down i container. A line had been drawn transversely across the plate at a point 11 cm from the lower edge of said plate. Test fluid (0.9% NaCl-solution) was poured into the container, until 20 mm of the plexiglass plate was located beneath the surface of the fluid. The test body was secured on the plexiglass plate so that the line drawn on the test body coincided with the line drawn on the plate while, at the same time, folding away the lower part of the test body so as to prevent it from coming into contact with the test liquid. A clock was started at the same time as the test body was laid onto the plate, with the test body extended down into the solution to the same extent as the plate. The increase in weight of the increase in weight of the test body with time was recorded.

Method 2. Measurements of Absorption Capacity and Degree of Utilization

A test product was secured in a fixture. Test fluid (0.9% NaCl-solution) was delivered to the wetting point of the product over a period of 60 minutes at the rate at which the fluid was absorbed. The amount of fluid absorbed was measured continuously and the total amount of fluid absorbed by the product constitutes the utilized absorption capacity of the test product. The test product was then placed in a fluid bath, in which it had the maximum opportunity of absorbing test fluid. The test product was then again weighed and the total absorption capacity calculated. The degree of utilization is given by the quotient between the utilized absorption capacity of the test product and the total absorption capacity.

Method 3. Determining Blood Absorption

A test body, 65×200 mm, was punched from the material. 5 ml test fluid (0.9% NaCl-solution) were delivered to the wetting point on the test body. Dispersion of the fluid was measured after about 30 minutes. A further 5 ml of test fluid (0.9% NaCl-solution) were then delivered to the wetting point and fluid dispersion was measured after about a further 30 minutes. Subsequent to the last delivery, eight filter papers were placed over the wetting point and loaded with a weight of 4.875 kg for 15 seconds. The filter papers were weighed both before and after applying the load and rewetting was recorded.

Test Results

Softening

With the intention of investigating how the material was affected at different softening roll spacings when softening the material, a material was tested under different softening conditions. For instance, in the case of a dry-formed CTMP-material having a weight per unit area of 900 g/m2 and a density of 0.63 g/cm3, a suitable roll spacing is 1.7–2.4 mm during the softening process. The material is not influenced to any great extent at roll spacings which lie within this range. FIG. 1 illustrates the absorption properties at different roll spacings. The results were determined in accordance with Method 1.

A Material according to the invention, roll spacing 1.7 mm.

B Material according to the invention, roll spacing 2.0 mm.

C Material according to the invention, roll spacing 2.4 mm.

D Material according to the invention, roll spacing 2.0 mm, softened twice.

E Material according to the invention, roll spacing 2.0 mm, softened four times.

F CTMP-pulp, density 0.125 g/cm3.

G Chemical sulphate pulp, density 0.125 g/cm3.

Absorption Properties of Absorbent Structures

Figure 2:
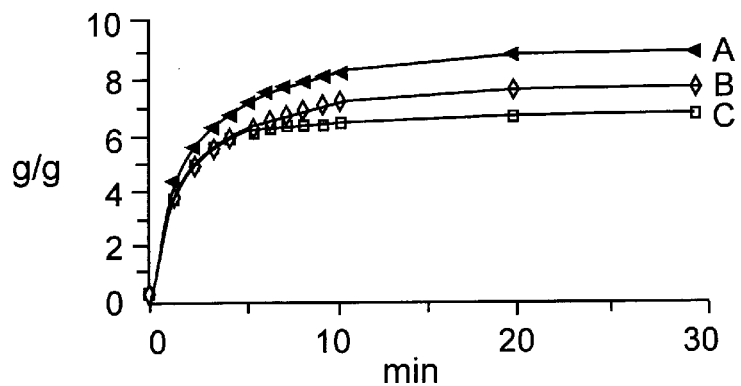
FIG. 2 illustrates the absorption properties of a dry-formed CTMP-material subsequent to being softened. Conventionally formed and compressed mats comprised of CTMP-pulp and chemical pulp respectively were used as references.

The absorption properties of an inventive CTMP-material having a weight per unit area of 900 g/m2 and a density of 0.63 g/cm3 compared with those of corresponding pulp cores produced from conventionally defibred and web-formed CTMP and corresponding chemical pulp are shown in FIG. 2. In the absence of superabsorbent material, the absorption capacity is about 9 g of fluid for each gram of absorbent material. The results were determined in accordance with Method 1.

A Material according to the invention.

B CTMP-pulp, density 0.125 g/cm3.

C Chemical sulphate pulp, density 0.125 g/cm3.

Admixing Superabsorbent Material

The presence of superabsorbent material in an absorbent body will influence the absorption properties of the body. Superabsorbent material can be incorporated in the absorbent body in different ways. For instance it may be admixed with the body material, laid in layers in the body, or disposed therein in some other way. This admixture of superabsorbent material can be effected in conjunction with manufacturing the dry-formed material, although it may also be effected during some other part of the manufacturing process. The absorption properties were compared with an inventive CTMP-material to which no superabsorbent material had been added and also with corresponding pulp cores comprised of conventional defibred CTMP and chemical pulp. The results were determined in accordance with Method 1.

A Chemical sulphate pulp containing 30% superabsorbent and having a density of 0.125 g/cm3.

B Inventive material containing 30% superabsorbent.

C Reference diaper containing 30% superabsorbent.

D Inventive material containing no superabsorbent.

Rewetting Measurements, Specific for Blood Absorption

In the case of blood absorption, products which comprised an inventive softened CTMP-material showed better rewetting values than non-softened products. The results also showed that when absorbing blood, products which lacked superabsorbent material exhibited lower rewetting values than material which contained superabsorbent material. Material which lacks superabsorbent material also disperses blood much more effectively. The reference products comprised two different products frequently found on the market. The results were determined in accordance with Method 3. The prerequisites for this effect are that at least one layer of the pulp mat is free from superabsorbent material. Of course, this does not exclude the presence of such material in other parts of the absorbent article.

A Inventive material 350 g/m2.

B Inventive material 350 g/m2, softened.

C Inventive material 350 g/m2 +5% superabsorbent.

D Inventive material 350 g/m2 +5% superabsorbent, softened.

A Reference product 1.

B Reference product 2.

C Product containing inventive material.

Network Strength

Dry-formed roll pulp will normally have sufficient mat strength for the product applications intended here. If the network strength of certain product applications should be found insufficient, the network strength can be increased by reinforcing the structure in some suitable manner, by adding reinforcing fibers, binding fibers or binding agent to the cellulose fiber mixture. The network strength can also be increased by incorporating a reinforcing layer of, for instance, plastic, non-woven, net or threads in the absorbent structure, or by fastening a reinforcing layer or an outer sheet on one or both sides of the material.

Density and Weight per Unit Area

The softened pulp mat is still very thin, and consequently it is unnecessary in many cases to further compress the mat prior to its use in an absorbent article. A suitable density is 0.2–1.0 g/cm3, preferably 0.3–0.9 g/cm3 and most preferably 0.6–0.8 g/cm3. A suitable weight per unit area is between 50–1000 g/m2, preferably 100–800 g/m2 and most preferably 200–600 g/cm2. When calculating the density, the thickness of the material was measured with the aid of a Mitutoyo thickness meter.

Description of a First Exemplifying Embodiment

Figure 3:
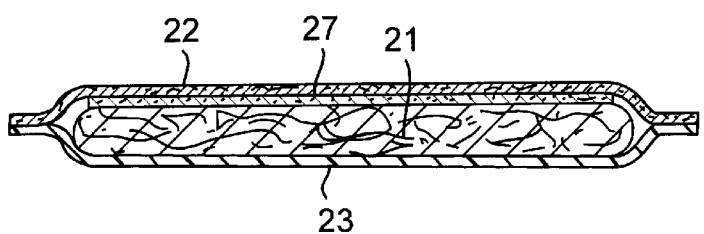
FIG. 3 illustrates an exemplifying embodiment of an inventive sanitary napkin.

FIG. 3 illustrates an exemplifying embodiment of an inventive sanitary napkin. The napkin comprises conventionally an absorbent body 21 which is enclosed between a fluid-permeable top sheet 22, which is suitably comprised of perforated plastic film or like material and which lies proximal to the wearer in use, and a fluid-impermeable bottom sheet 23. A thin fluid-permeable layer 27, for instance of nonwoven material, may be placed between the absorbent body 21 and the top sheet 22. The sheets 22 and 23 have parts which protrude beyond the absorbent body 21 and the sheets are mutually joined at these protruding parts. The bottom sheet 23 is comprised of a suitable plastic material, for instance polyethylene. It will be understood, however, that other known materials may be used for the top and the bottom sheets within the scope of the invention.

The absorbent body 21 is comprised of one single layer. This layer may consist of a dry-formed material according to the invention which contains from 0–10% superabsorbent material. A suitable density range in the case of the absorbent body 21 is 0.6–0.9 g/cm3, while a suitable weight per unit area is 200–300 g/m2. When the absorbent body is comprised of a CTMP-material or some other material having a yellowish or brownish colour, a covering layer of chemical pulp white in colour may be applied to the top of the absorbent body.

Description of a Second Exemplifying Embodiment

Figure 4:
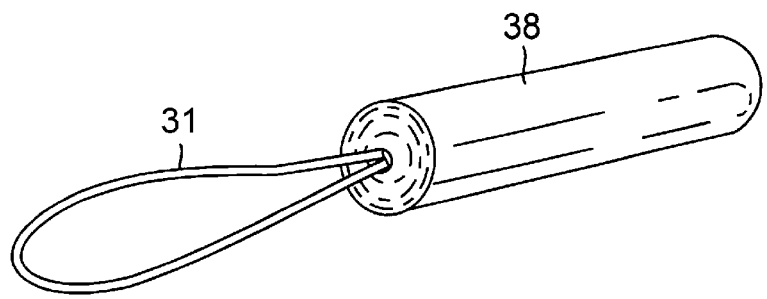
FIG. 4 illustrates an exemplifying embodiment of an inventive tampon.

FIG. 4 illustrates an exemplifying embodiment of an inventive tampon. The tampon is comprised of an inventive absorbent material which has been rolled to a cylinder-like form 31. In conjunction with rolling the absorbent material into its cylindrical shape, a string 38 is placed in the center of the cylinder 31, in a conventional manner, and the cylinder 31 is compressed to the desired thickness and shape, in a conventional manner. Prior to being compressed and shaped, the absorbent material will suitably have a density range of 0.4–0.9 g/cm3 and a suitable per unit area weight of 200–600 g/m2.

Description of a Third Exemplifying Embodiment

Figure 5:
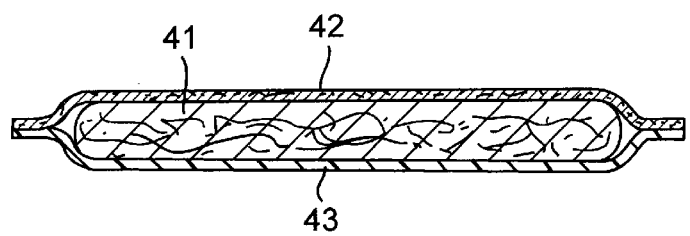
FIG. 5 illustrates an exemplifying embodiment of an inventive dressing.

FIG. 5 illustrates an exemplifying embodiment of an inventive wound or sore dressing. The dressing includes, in a conventional manner, an absorbent body 41 which is enclosed between a fluid-permeable top sheet 42, which is suitably comprised of a soft non-woven material, a perforated plastic film or the like, and which is intended to lie proximal to the wearer in use, and a fluid-repellent bottom sheet 43. The sheets 42 and 43 have parts which protrude beyond the absorbent body 41 and are joined together at these protruding parts. The bottom sheet 43 is comprised of a suitable fluid-repellent material, for instance a non-woven material that has been made hydrophobic. It will be understood, however, that the top and bottom sheets may comprise other known materials, within the scope of the invention.

The absorbent body 41 is comprised of only one single layer. This layer may consist of inventive dry-formed material and may be constructed with a relatively open fiber structure of relatively low density and with a superabsorbent content of 0–10%. A suitable density range in respect of the absorbent body 41 is 0.20–0.50 g/cm3 and a suitable weight per unit area is 200–700 g/m2.

It will be understood that the invention is not restricted to the illustrated and described exemplifying embodiments thereof and that other embodiments are conceivable within the scope of the following claims.

We claim:

1. A method for manufacturing an absorbent structure in an absorbent article, comprising:

flash drying paper pulp into flash-dried cellulose fibers, dry-forming particulate material to a web with a weight per unit area of between 30–1000 g/m$^2$, 30–100% of the particulate material including the flash-dried cellulose fibers, compressing said web to a web density of between 0.2–1.0 g/cm$^3$, mechanically softening and delaminating the web, and incorporating said mechanically softened and delaminated web as an absorbent structure in an absorbent article without subsequent defibration and fluffing.

2. The method for manufacturing an absorbent structure according to claim 1, comprising compressing said web to a web density of between 0.3–0.9 g/cm$^3$.

3. The method for manufacturing an absorbent structure according to claim 1, comprising compressing said web to a web density of between 0.6–0.8 g/cm$^3$.

4. The method for manufacturing an absorbent structure according to claim 1, wherein the mechanically softening and therewith delaminating said web before incorporating it as an absorbent structure in an absorbent article, achieves in said web a plurality of partially separated thin fiber layers, which in themselves exhibit a density which corresponds to said web density.

5. The method of claim 1, wherein the absorbent article is a diaper, sanitary napkin, panty protector, incontinence guard, bed protector, a wound or sore dressing, or saliva absorbent.

6. An absorbent structure in an absorbent article, wherein the structure has been manufactured according to the method claimed in claim 1.

7. The absorbent structure according to claim 6, wherein the weight per unit area of the structure is between 100–800 g/m$^2$.

8. The absorbent structure according to claim 6, wherein said cellulose fibers are mainly comprised of fibers of chemi-thermomechanically produced pulp.

9. The absorbent structure according to claim 8, wherein said chemi-thermomechanical pulp fibers have a curl value of between 0.20 and 0.40.

10. The absorbent structure according to claim 6, wherein some of said fibers are chemically stiffened cellulose fibers.

11. The absorbent structure according claim 6, wherein the structure includes reinforcing means.

12. The absorbent structure of claim 6, wherein the absorbent article is a diaper, sanitary napkin, panty protector, incontinence guard, bed protector, a wound or sore dressing, or saliva absorbent.

13. The absorbent structure of claim 11, wherein the reinforcing means is a binding agent, reinforcing fibers, or thermoplastic binding fibers.

14. The absorbent structure according to claim 6, wherein the structure includes a reinforcing layer.

15. The absorbent structure according to claim 14, wherein the reinforcing layer includes nonwoven, tissue, plastic, or net material.

16. An absorbent article, comprising a liquid-permeable top sheet, an essentially liquid-impermeable bottom sheet, and an absorbent body which includes an absorbent structure according to claim 6 enclosed between said sheets.

17. The absorbent article according to claim 16, wherein said absorbent structure is covered with a layer of chemical pulp on one side thereof.

18. The absorbent article of claim 16, wherein the absorbent article is a diaper, sanitary napkin, panty protector, incontinence guard, bed protector, a wound or sore dressing, or saliva absorbent.

19. An absorbent article for absorbing blood, comprising an absorbent structure according to claim 6.

20. The absorbent article according to claim 19, wherein the absorbent article is a tampon.

21. The absorbent article according to claim 16, wherein said absorbent structure is mainly comprised of fibers of chemi-thermomechanically produced pulp, the article including between 0–15% superabsorbent material, calculated on a total weight of the structure in a dry state.

22. The use, in absorbent structures incorporated in absorbent articles, such as diapers, sanitary napkins, tampons, panty protectors, incontinence guards, bed protectors, wound or sore dressings, saliva absorbents and like articles, of a web dry-formed of particulate material containing 30–100% flash-dried cellulose fibers to a web with a weight per unit area of 30–1000 $g/m^2$ compressed to a density of 0.2–1.0 $g/cm^3$, and mechanically softened and delaminated before incorporation as the absorbent structure, without any subsequent defibration and fluffing.

* * * * *